(12) United States Patent
Reddy

(10) Patent No.: US 10,751,526 B2
(45) Date of Patent: Aug. 25, 2020

(54) SUBCUTANEOUS LEAD IMPLANTATION

(71) Applicant: CARDIAC PACEMAKERS, INC., St. Paul, MN (US)

(72) Inventor: G. Shantanu Reddy, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 120 days.

(21) Appl. No.: 16/169,383

(22) Filed: Oct. 24, 2018

(65) Prior Publication Data
US 2019/0117959 A1 Apr. 25, 2019

Related U.S. Application Data

(60) Provisional application No. 62/576,910, filed on Oct. 25, 2017.

(51) Int. Cl.
| | |
|---|---|
| *A61N 1/05* | (2006.01) |
| *A61N 1/375* | (2006.01) |
| *A61B 17/34* | (2006.01) |
| *A61N 1/39* | (2006.01) |
| *A61B 17/32* | (2006.01) |

(52) U.S. Cl.
CPC ........ *A61N 1/0504* (2013.01); *A61B 17/3468* (2013.01); *A61N 1/057* (2013.01); *A61N 1/3752* (2013.01); *A61N 1/3956* (2013.01); *A61B 2017/320056* (2013.01); *A61N 1/0563* (2013.01); *A61N 2001/058* (2013.01)

(58) Field of Classification Search
CPC .... A61B 17/3468; A61B 2017/320056; A61N 1/0504; A61N 1/0563; A61N 1/057; A61N 1/3752; A61N 1/3956; A61N 2001/058
See application file for complete search history.

(56) References Cited

U.S. PATENT DOCUMENTS

| | | |
|---|---|---|
| 4,716,888 A | 1/1988 | Wesner |
| 5,300,106 A | 4/1994 | Dahl et al. |
| 6,647,292 B1 | 11/2003 | Bardy et al. |
| 6,721,597 B1 | 4/2004 | Bardy et al. |
| 7,149,575 B2 | 12/2006 | Ostroff et al. |
| 7,194,302 B2 | 3/2007 | Bardy et al. |
| 7,248,921 B2 | 7/2007 | Palreddy et al. |
| 7,299,092 B2 | 11/2007 | Bardy et al. |
| 7,376,458 B2 | 5/2008 | Palreddy et al. |
| 7,392,085 B2 | 6/2008 | Warren et al. |
| 7,477,935 B2 | 1/2009 | Palreddy et al. |
| 7,493,175 B2 | 2/2009 | Cates et al. |

(Continued)

OTHER PUBLICATIONS

International Search Report and Written Opinion dated Nov. 15, for International Application No. PCT/US2018/046852.

(Continued)

*Primary Examiner* — George Manuel
(74) *Attorney, Agent, or Firm* — Seager, Tufte & Wickhem LLP

(57) ABSTRACT

Methods and kits for subcutaneous defibrillator implantation. In various examples, two introducer tools each having a sheath are used during an implantation procedure to obviate the need for pulling a lead using a suture. The elimination of the suture-based pulling steps may reduce procedure time. A kit having two introducer tool and corresponding sheaths is also disclosed.

20 Claims, 15 Drawing Sheets

(56) References Cited

U.S. PATENT DOCUMENTS

| | | |
|---|---|---|
| 7,623,909 B2 | 11/2009 | Sanghera et al. |
| 7,655,014 B2 | 2/2010 | Ko et al. |
| 8,019,443 B2 | 9/2011 | Schleicher et al. |
| 8,157,813 B2 | 4/2012 | Ko et al. |
| 8,160,686 B2 | 4/2012 | Allavatam et al. |
| 8,160,687 B2 | 4/2012 | Warren et al. |
| 8,200,341 B2 | 6/2012 | Sanghera et al. |
| 8,244,377 B1 | 8/2012 | Pianca et al. |
| 8,285,397 B2 | 10/2012 | Grandhe |
| 8,332,043 B1 | 12/2012 | Jaax et al. |
| 8,483,841 B2 | 7/2013 | Sanghera et al. |
| 8,483,843 B2 | 7/2013 | Sanghera et al. |
| 8,532,789 B2 | 9/2013 | Smits |
| 8,565,878 B2 | 10/2013 | Allavatam et al. |
| 8,718,793 B2 | 5/2014 | O'Connor |
| 8,801,729 B2 | 8/2014 | Ko et al. |
| 9,079,035 B2 | 7/2015 | Sanghera et al. |
| 9,216,284 B2 | 12/2015 | O'Connor |
| 9,381,030 B2 | 7/2016 | Geroy |
| 9,610,435 B2 | 4/2017 | Schleicher et al. |
| 9,610,436 B2 | 4/2017 | Seifert et al. |
| 9,981,121 B2 | 5/2018 | Seifert et al. |
| 10,391,325 B2 | 8/2019 | De Kock et al. |
| 2003/0187460 A1 | 10/2003 | Chin et al. |
| 2004/0230272 A1 | 11/2004 | Cates et al. |
| 2004/0230279 A1 | 11/2004 | Cates et al. |
| 2006/0126676 A1 | 6/2006 | Hollemann et al. |
| 2008/0208247 A1 | 8/2008 | Rutten et al. |
| 2009/0125059 A1 | 5/2009 | Verzal et al. |
| 2009/0210043 A1 | 8/2009 | Reddy |
| 2010/0030311 A1 | 2/2010 | Lazeroms et al. |
| 2010/0125194 A1 | 5/2010 | Bonner et al. |
| 2011/0054580 A1 | 3/2011 | Desai et al. |
| 2011/0054581 A1 | 3/2011 | Desai et al. |
| 2012/0029335 A1 | 2/2012 | Sudam et al. |
| 2013/0131767 A1 | 5/2013 | Desai et al. |
| 2014/0144580 A1 | 5/2014 | Desai et al. |
| 2014/0194963 A1 | 7/2014 | Desai et al. |
| 2014/0200592 A1 | 7/2014 | O'Connor |
| 2014/0330248 A1 | 11/2014 | Thompson-Nauman et al. |
| 2014/0330327 A1 | 11/2014 | Thompson-Nauman et al. |
| 2015/0105793 A1 | 4/2015 | Cole |
| 2015/0133951 A1 | 5/2015 | Seifert et al. |
| 2015/0209077 A1 | 7/2015 | Marshall |
| 2015/0343176 A1 | 12/2015 | Aselson et al. |
| 2015/0343197 A1* | 12/2015 | Gardeski .................. A61N 1/05 606/129 |
| 2015/0352352 A1 | 12/2015 | Soltis et al. |
| 2016/0339233 A1 | 11/2016 | De Kock et al. |
| 2017/0020551 A1 | 1/2017 | Reddy et al. |
| 2017/0021159 A1 | 1/2017 | Reddy et al. |
| 2017/0095657 A1 | 4/2017 | Reddy et al. |
| 2017/0100148 A1 | 4/2017 | De Kock et al. |
| 2017/0319845 A1 | 11/2017 | De Kock et al. |
| 2017/0319864 A1 | 11/2017 | De Kock et al. |
| 2018/0036527 A1 | 2/2018 | Reddy et al. |
| 2018/0036547 A1 | 2/2018 | Reddy |
| 2018/0133458 A1 | 5/2018 | Foster et al. |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0193060 A1 | 7/2018 | Reddy et al. |
| 2018/0214686 A1 | 8/2018 | De Kock et al. |
| 2018/0296824 A1 | 10/2018 | De Kock et al. |
| 2018/0344200 A1 | 12/2018 | Thakur et al. |
| 2018/0344252 A1 | 12/2018 | An et al. |
| 2019/0054289 A1 | 2/2019 | Reddy et al. |
| 2019/0054290 A1 | 2/2019 | De Kock et al. |
| 2019/0117959 A1 | 4/2019 | Reddy |
| 2019/0151651 A1 | 5/2019 | Reddy et al. |

OTHER PUBLICATIONS

Darrat et al; "Single Incision Technique for Placement of Subcutaneous Implantable Cardioverter Defibrillators," http://abstractsonline.com/pp8/, accessed May 14, 2018.

Boston Scientific, "Users Manual Emblem S-ICD", pp. 1-19, 2015.

Cameron Health, "A Patient Guide—Living With Your S-ICD System," pp. 1-47, 2012.

* cited by examiner

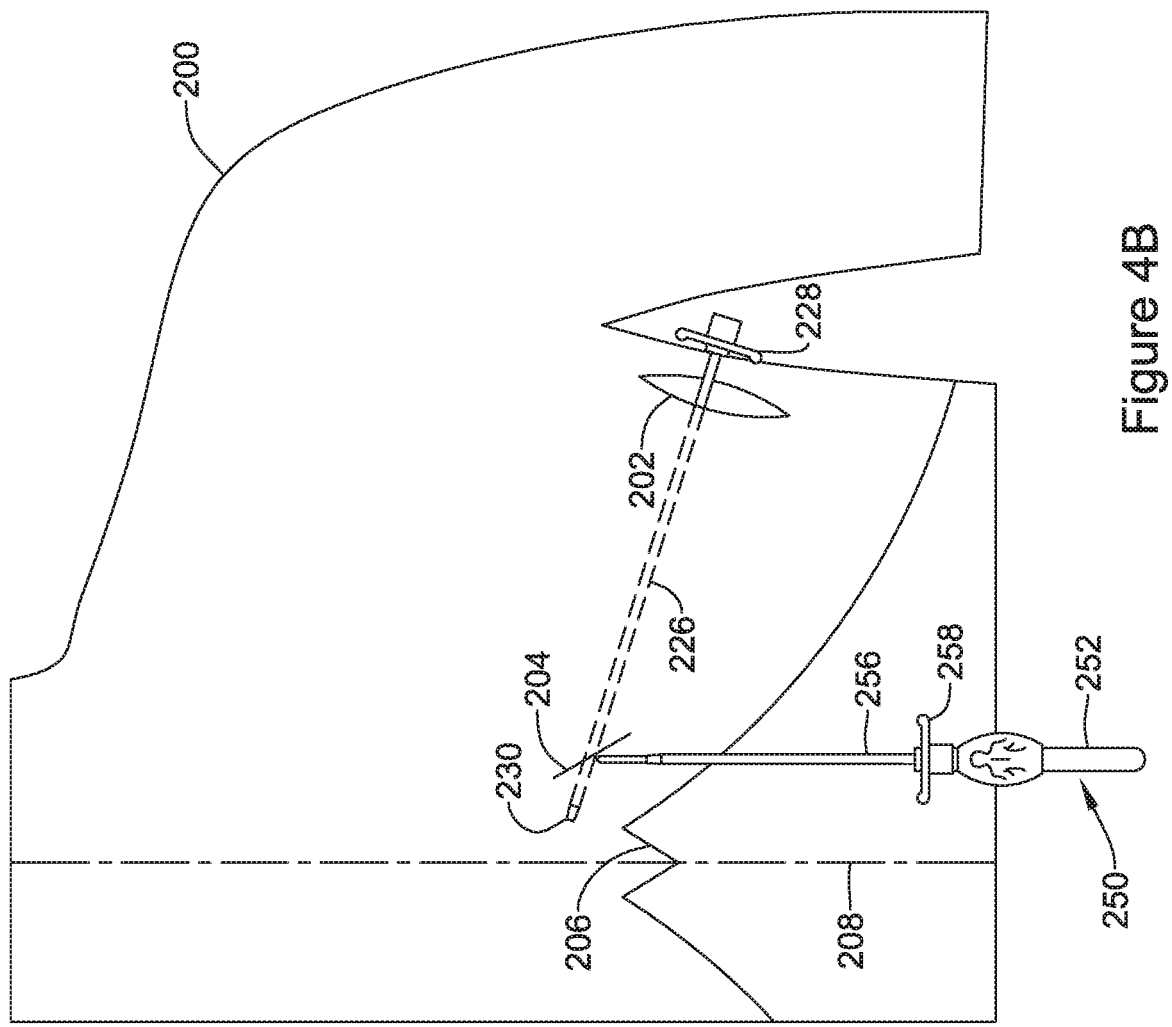

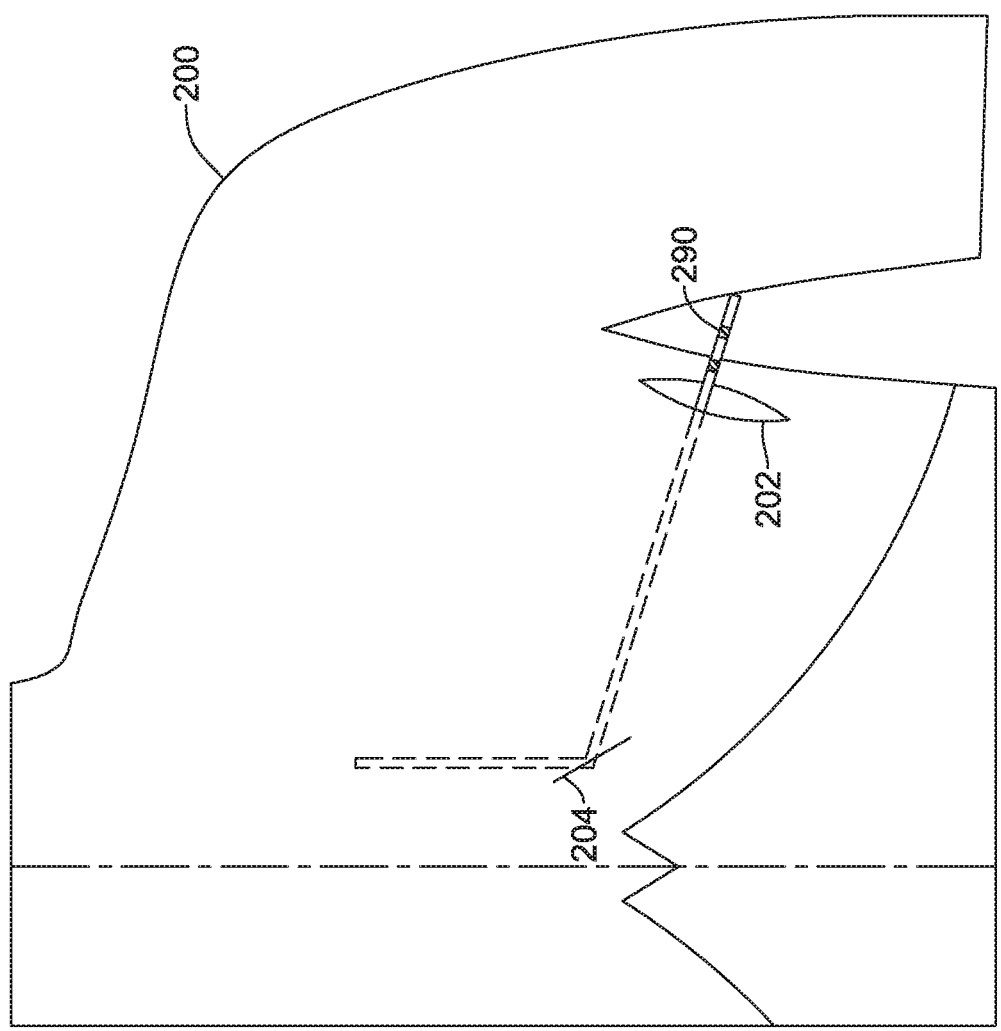

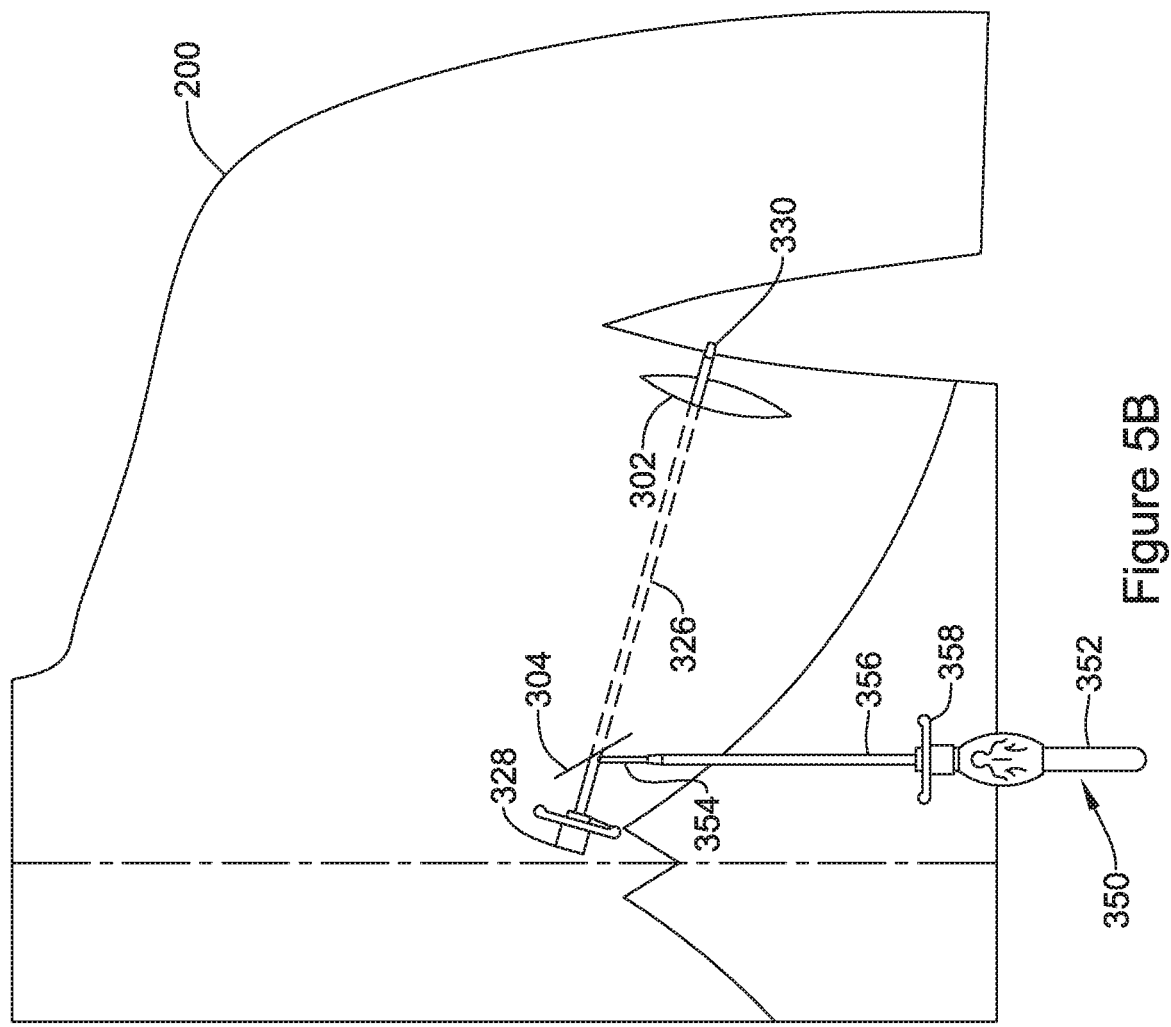

SUBCUTANEOUS LEAD IMPLANTATION

CROSS REFERENCE TO RELATED APPLICATIONS

The present application claims the benefit of and priority to U.S. Provisional Patent Application Ser. No. 62/576,910, filed on Oct. 25, 2017, and titled SUBCUTANEOUS LEAD IMPLANTATION, the disclosure of which is incorporated herein by reference.

BACKGROUND

The subcutaneous implantable cardioverter defibrillator (S-ICD System™) from Boston Scientific Corporation has been commercially available in many countries for several years now. The commercial system and implant comprises a pulse generator implanted on the left side of the chest, near the left axilla, with a lead extending from the left axilla to near the xiphoid process and then superiorly just to the left of the sternum, over the ribs. The implant method has been updated several times from early implants to current practices.

The most common implant practice has been to use a three incision method. A tunneling tool is advanced from a xiphoid incision to an incision at the left axilla. A long loop of suture is used to secure the lead distal tip to the tunneling end of the tunneling tool. The tunneling tool is slowly withdrawn via the xiphoid incision, pulling the lead into the xiphoid-axillary tunnel by the suture until the distal end of the lead exits the xiphoid incision. Next, the tunneling tool is advanced from the xiphoid incision to an upper sternal incision near but generally inferior to the manubrium, with the suture still attached. The suture loop should be long enough to allow this parasternal tunnel to be formed without the lead having to go into the tissue.

After the distal dip of the tunneling tool exits the upper sternal incision, the suture loop is cut and the ends of the suture loop extending out of the upper sternal incision are grasped with a forceps. The tunneling tool is removed. The distal tip of the lead is pulled into the parasternal tunnel using the suture grasped by the forceps until the distal tip of the lead exits the upper sternal incision. The suture loop is removed and discarded. The lead is sutured to the fascia at the upper sternal incision, and a suture sleeve is placed over the lead near the xiphoid incision to provide additional fixation.

A two incision approach has also been considered and used. In a two incision approach, the lead may be pulled from the left axilla through a subcutaneous tunnel to the xiphoid incision similar to the three incision approach. An introducer with a sheath thereon may be advanced from the xiphoid incision superiorly alongside the sternum. The introducer is then removed while holding the sheath in place, with the sheath acting to preserve the tunneled route for placement of the lead. The lead is inserted through the sheath, and the sheath is removed while holding the lead in place. A suture sleeve is used to anchor the lead at the xiphoid incision. The two incision approach does not include an upper sternal incision, thereby reducing the number of scars, improving the cosmetic outcome and potentially reducing infection risk.

In each of these methods of implantation, there is a significant amount of time spent tying knots with sutures to, for example, couple together the lead with the implantation tool, to tie to the lead itself for the "pulling" steps, to suture the lead down to the fascia, and to attach the lead and suture sleeve combined to the fascia. Reducing the amount of knot tying would reduce procedure time.

When first introduced, an anticipated benefit of the S-ICD System™ was that of reduced procedure time. Some implanters have been able to see benefits in that regard. However, years of experience have shown that with the methods described above, even after several rounds of enhancement and continued physician training updates, procedure time benefits have not been broadly realized. There is continuing interest in new and different methods that can reduce procedure time.

Overview

The present inventors have recognized, among other things, that a problem to be solved is the continuing need for new and alternative approaches to subcutaneous lead implantation.

A first illustrative, non-limiting example takes the form of a method of implanting a subcutaneous-only defibrillator system in a patient, the system comprising a pulse generator having a lead port and a lead having a proximal end to attach to the pulse generator lead port and a distal end with at least one electrode thereon, the method comprising: making an axillary incision near the left axilla; making a xiphoid incision near the xiphoid; inserting a first introducer tool and first sheath, with the first sheath removably disposed on the first introducer tool, through one of the axilla or xiphoid incisions to create a first tunnel to the other of the xiphoid or axilla incisions; removing the first introducer tool and leaving the first sheath in place between the axilla and xiphoid incisions; inserting the proximal end of the lead into the first sheath and advancing the proximal end of the lead from the xiphoid incision to and through the axillary incision through the first sheath; removing the first sheath while maintaining the lead in a position such that the proximal end of the lead extends out of the axillary incision and the distal end of the lead extends out of the xiphoid incision with a portion of the lead disposed in the first tunnel; inserting a second introducer tool and second sheath, with the second sheath removably disposed on the second introducer tool, through the xiphoid incision in a generally cephalad direction to create a second tunnel alongside or parallel to the sternum; removing the second introducer tool and leaving the second sheath in place in the second tunnel; inserting the distal end of the lead into the second sheath and advancing the distal end of the lead to a desired position; and removing the second sheath while maintaining a portion of the lead in the second tunnel.

Additionally or alternatively to the first illustrative, non-limiting example, the method may be such that the first introducer tool has a proximal end with a handle and a tunneling shaft extending from the handle to a distal tip; the first sheath has a proximal end with a hub and a distal end having a length such that, when the first sheath is removably disposed on the first introducer tool, the hub is adjacent the handle and the distal end of the first sheath is proximal of the distal tip of the first introducer tool; the step of inserting the first introducer tool and the first sheath is performed by inserting the distal end of the first introducer tool into the axillary incision and advancing the distal end of the first introducer tool to and through the xiphoid incision until the distal end of the first sheath extends out of the xiphoid incision; and the step of inserting the proximal end of the lead into the first sheath is performed by passing the proximal end of the lead through the distal end of the first sheath and advancing the lead therein until the proximal end of the lead extends out of the hub of the first sheath and the axillary incision.

Additionally or alternatively to the first illustrative, non-limiting example, the method may be such that the first introducer tool has a proximal end with a handle and a tunneling shaft extending from the handle to a distal tip; the first sheath has a proximal end with a hub and a distal end having a length such that, when the first sheath is removably disposed on the first introducer tool, the hub is adjacent the handle and the distal end of the first sheath is proximal of the distal tip of the first introducer tool; the step of inserting the first introducer tool and the first sheath is performed by inserting the distal end of the first introducer tool into the xiphoid incision and advancing the distal end of the first introducer tool to and through the axillary incision until the distal end of the first sheath extends out of the axillary incision; and the step of inserting the proximal end of the lead into the first sheath is performed by passing the proximal end of the lead through the hub of the first sheath and advancing the lead therein until the proximal end of the lead extends out of the distal end of the first sheath and the axillary incision.

Additionally or alternatively to the first illustrative, non-limiting example or above variants thereon, the method may further comprise using one or more sutures to secure the lead in place at the xiphoid incision.

Additionally or alternatively to the first illustrative, non-limiting example or above variants thereon, the lead may comprise one or more anchoring structures thereon at an intermediate location between the at least one electrode and the proximal end, the anchoring structure configured to anchor the lead in position near the xiphoid incision.

Additionally or alternatively to the first illustrative, non-limiting example and the above variants thereon, the method may further comprise applying one or more sutures at the anchoring structure to anchor the lead in position at the xiphoid incision.

Additionally or alternatively to the first illustrative, non-limiting example or above variants thereon, the anchoring structure may include one or more tines or hooks extending therefrom to secure to patient tissue for holding the lead in a desired position.

Additionally or alternatively to the first illustrative, non-limiting example and the above variants thereon, the method may further comprise inserting the proximal end of the lead in the lead port, and inserting the pulse generator through the axillary incision to implant the pulse generator in the patient.

Additionally or alternatively to the first illustrative, non-limiting example or above variants thereon, the lead may comprise one or more anchoring structures at the distal tip thereof, the anchoring structures comprising one or more of a tine or a hook.

Additionally or alternatively to the first illustrative, non-limiting example or above variants thereon, the step of removing the first sheath may be performed after the step of removing the second introducer tool.

Additionally or alternatively to the first illustrative, non-limiting example or above variants thereon, the step of removing the first sheath may be performed before the step of removing the second introducer tool.

A second illustrative, non-limiting example takes the form of a method of implanting a subcutaneous-only defibrillator system in a patient, the system comprising a pulse generator having a lead port and a lead having a proximal end to attach to the pulse generator lead port and a distal end with at least one electrode thereon, the method comprising: making an axillary incision near the left axilla; making a xiphoid incision near the xiphoid; inserting a first introducer tool and first sheath, with the first sheath removably disposed on the first introducer tool, through one of the axilla or xiphoid incisions to create a first tunnel to the other of the xiphoid or axilla incisions; removing the first introducer tool and leaving the first sheath in place between the axilla and xiphoid incisions; inserting the distal end of the lead into the first sheath and advancing the distal end of the lead from the axillary incision to and through the xiphoid incision through the first sheath; removing the first sheath while maintaining the lead in a position such that the proximal end of the lead extends out of the axillary incision and the distal end of the lead extends out of the xiphoid incision with a portion of the lead disposed in the first tunnel; inserting a second introducer tool and second sheath, with the second sheath removably disposed on the second introducer tool, through the xiphoid incision in a generally cephalad direction to create a second tunnel alongside or parallel to the sternum; removing the second introducer tool and leaving the second sheath in place in the second tunnel; inserting the distal end of the lead into the second sheath and advancing the distal end of the lead to a desired position; and removing the second sheath while maintaining a portion of the lead in the second tunnel.

Additionally or alternatively to the second illustrative, non-limiting example, the method may be such that the first introducer tool has a proximal end with a handle and a tunneling shaft extending from the handle to a distal tip; the first sheath has a proximal end with a hub and a distal end having a length such that, when the first sheath is removably disposed on the first introducer tool, the hub is adjacent the handle and the distal end of the first sheath is proximal of the distal tip of the first introducer tool; the step of inserting the first introducer tool and the first sheath is performed by inserting the distal end of the first introducer tool into the axillary incision and advancing the distal end of the first introducer tool to and through the xiphoid incision until the distal end of the first sheath extends out of the xiphoid incision; and the step of inserting the distal end of the lead into the first sheath is performed by passing the distal end of the lead through the hub of the first sheath and advancing the lead therein until the distal end of the lead extends out of the distal end of the first sheath and the xiphoid incision.

Additionally or alternatively to the second illustrative, non-limiting example, the method may be such that the first introducer tool has a proximal end with a handle and a tunneling shaft extending from the handle to a distal tip; the first sheath has a proximal end with a hub and a distal end having a length such that, when the first sheath is removably disposed on the first introducer tool, the hub is adjacent the handle and the distal end of the first sheath is proximal of the distal tip of the first introducer tool; the step of inserting the first introducer tool and the first sheath is performed by inserting the distal end of the first introducer tool into the xiphoid incision and advancing the distal end of the first introducer tool to and through the axillary incision until the distal end of the first sheath extends out of the axillary incision; and the step of inserting the distal end of the lead into the first sheath is performed by passing the distal end of the lead into the distal end of the first sheath and advancing the lead therein until the distal end of the lead extends out of the hub of the first sheath and the axillary incision.

Additionally or alternatively to the second illustrative, non-limiting example or above variants thereon, the method may further comprise using one or more sutures to secure the lead in place at the xiphoid incision.

Additionally or alternatively to the second illustrative, non-limiting example or above variants thereon, the lead may comprise one or more anchoring structures thereon at an intermediate location between the at least one electrode and the proximal end, the anchoring structure configured to anchor the lead in position near the xiphoid incision.

Additionally or alternatively to the second illustrative, non-limiting example or above variants thereon, the method may further comprise applying one or more sutures at the anchoring structure to anchor the lead in position at the xiphoid incision.

Additionally or alternatively to the second illustrative, non-limiting example or above variants thereon, the anchoring structure may include one or more tines or hooks extending therefrom to secure to patient tissue for holding the lead in a desired position.

Additionally or alternatively to the second illustrative, non-limiting example or above variants thereon, the method may further comprise inserting the proximal end of the lead in the lead port, and inserting the pulse generator through the axillary incision to implant the pulse generator in the patient.

Additionally or alternatively to the second illustrative, non-limiting example or above variants thereon, the lead may comprise one or more anchoring structures at the distal tip thereof, the anchoring structures comprising one or more of a tine or a hook.

Additionally or alternatively to the second illustrative, non-limiting example or above variants thereon, the step of removing the first sheath may be performed after the step of removing the second introducer tool.

Additionally or alternatively to the second illustrative, non-limiting example or above variants thereon, the step of removing the first sheath may be performed before the step of removing the second introducer tool.

A third illustrative, non-limiting example takes the form of an implantation tool kit for implantation of a medical device comprising: a first introducer tool having a proximal end with a handle and a tunneling shaft extending from the handle to a distal tip, the tunneling shaft having a first length; a first sheath has a proximal end with a hub and a distal end and having a second length such that, when the first sheath is removably disposed on the first introducer tool, the hub is adjacent the handle and the distal end of the first sheath is proximal of the distal tip of the first introducer tool; a second introducer tool having a proximal end with a handle and a tunneling shaft extending from the handle to a distal tip, the tunneling shaft having a third length; a second sheath has a proximal end with a hub and a distal end and having a fourth length such that, when the second sheath is removably disposed on the second introducer tool, the hub is adjacent the handle and the distal end of the second sheath is proximal of the distal tip of the second introducer tool; wherein the first length is greater than the second length.

Additionally or alternatively to the third illustrative, non-limiting example, the first length may be adapted for use in establishing a first tunnel from a position near the xiphoid to the left axilla of a patient, and the handle of the first introducer tool may include a marking designating that the first introducer tool is for use in establishing the first tunnel; and the second length may be adapted for use in establishing a second tunnel from a position near the xiphoid cephalad within a patient for at least 10 cm, and the handle of the second introducer tool may include a marking designating that the second introducer tool is for use in establishing the second tunnel.

Additionally or alternatively to the third illustrative, non-limiting example, the first length may be in the range of about 20 to about 40 cm; the first sheath may be sized to leave about 1-4 cm of the distal tip of the first introducer tool uncovered when the first sheath is disposed thereon; the second length may be in the range of about 12 to about 20 cm; and the second sheath may be sized to leave about 1-3 cm of the distal tip of the second introducer tool uncovered when the second sheath is disposed thereon.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

FIGS. 4A-4E illustrate several implantation steps and methods using tools as in FIG. 3;

FIGS. 5A-5E illustrate several additional implantation steps and methods using tools as in FIG. 3;

DETAILED DESCRIPTION

Figure 1:
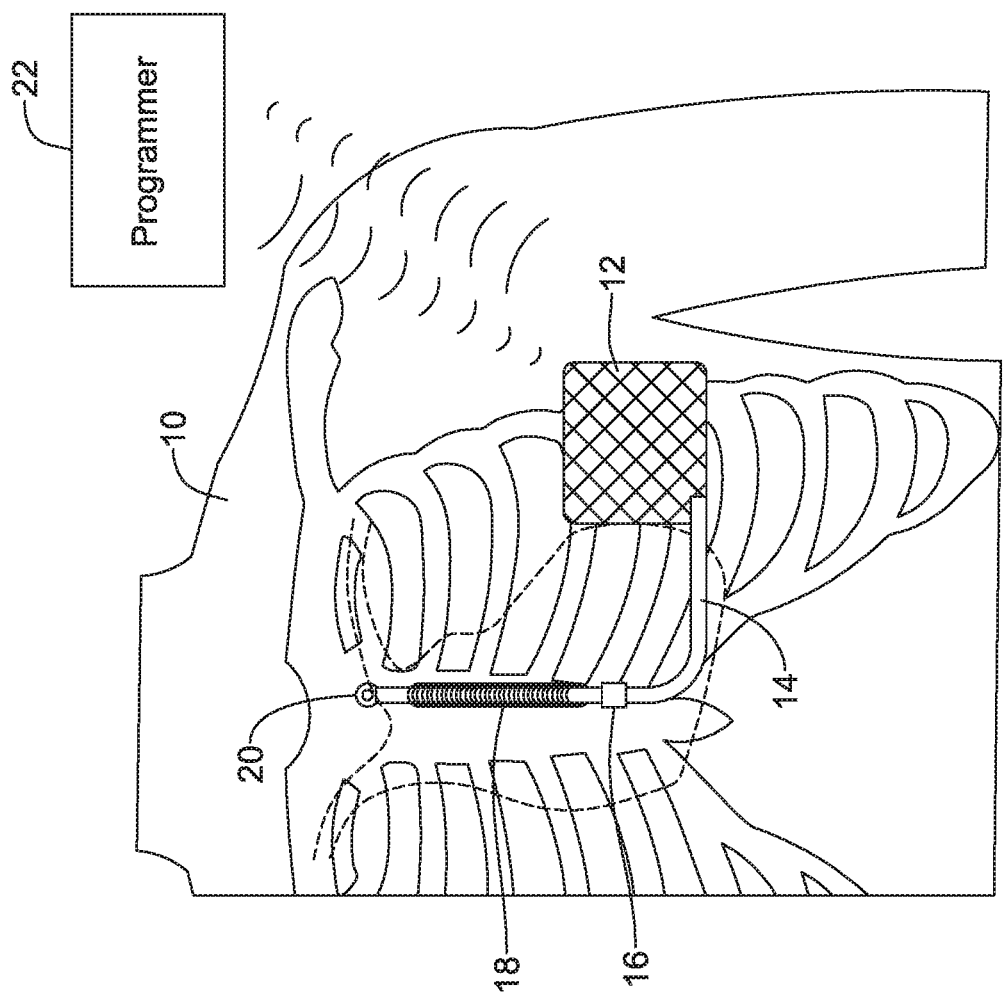
FIG. 1 shows an illustrative implant position for a subcutaneous defibrillator.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 shows an illustrative implant position for a subcutaneous defibrillator. The patient 10 is shown having an implanted pulse generator 12 that attaches to a lead 14. The lead 14 has a proximal end that removably attaches to the pulse generator 12 and a distal end with three electrodes—a proximal ring electrode 16, an intermediate coil electrode 18, and a distal tip electrode 20. In the commercial implementation, the coil electrode 18 and the housing of the pulse generator 12 are used for delivery of high voltage shocks in response to identified ventricular arrhythmia, as well as to deliver induction testing signals and post-shock pacing. Also in the commercial implementation, the housing of the pulse generator 12 is used along with the proximal ring electrode 16 and distal tip electrode 20 for sensing cardiac signals. If implanted according to the directions for use, the pulse generator 12 will be approximately at the midline of the axilla, and the portion of the lead having the electrodes 16, 18, 20, would extend about 1-2 cm to the left of the sternum.

Other implant positions may be used instead of those shown, such as with the lead extending to the posterior of the patient instead of across the anterior chest, or with the lead extending to the right side of the sternum. Various publications have found that having the lead very near the sternum, generally in a straight line, with the pulse generator at a lateral position along the axillary midline, tends to improve defibrillation performance. Also helpful is ensuring that implantation of all electrodes 16, 18, 20 and the pulse generator 12 is performed close to the fascia—that is, as far into the subcutaneous tissue as can be achieved. Some work has been done on implanting the pulse generator between the ribs and the fascia and/or beneath certain muscle groups, each of which adds to the surgical challenge of implantation but may provide benefits for system performance and cosmetic appearance post-implant.

Detailed discussions of various features of the S-ICD™ System may be found in a number of patents and publications. For example, U.S. Pat. Nos. 6,721,597, 7,149,575, 8,157,813, 8,483,841, and 9,079,035, as well as US PG Patent Pub. No. 20120029335, the disclosures of which are incorporated herein by reference, show a variety of implantation locations, methods, and lead designs. U.S. Pat. Nos. 7,248,921, 7,392,085, 7,376,458, 7,477,935, 7,623,909, 8,160,686, 8,160,687, 8,200,341, 8,483,843, and 8,565,878, the disclosures of which are also incorporated herein by reference, describe a variety of methods and devices for configuring device sensing, sensing cardiac events, analyzing beats and rhythms, and making therapy decisions. The present invention relates to systems that may relate to or incorporate features and methods disclosed in these patent applications, though other implementation may be used instead.

Figure 2:
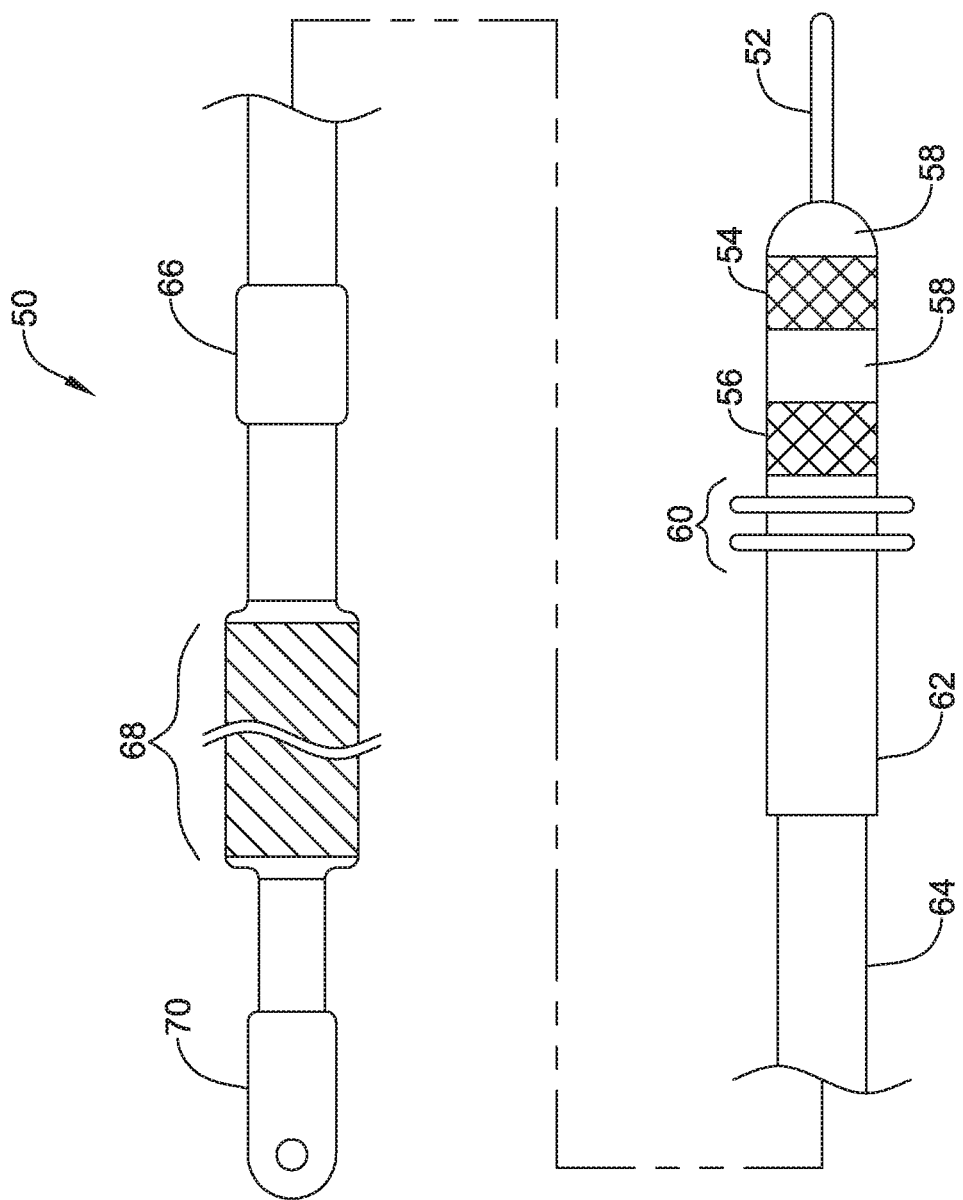
FIG. 2 shows an illustrative implantable lead.

FIG. 2 shows an illustrative implantable lead. The lead 50 has at its proximal end a plug configuration for securing to a pulse generator, including a core wire 52, connector rings 54, 56, insulation rings 58, and seals 60. A sheath 62 covers a proximal portion of the lead body 64. The distal end of the lead 50 comprises the proximal sense ring electrode 66, a coil electrode 68, and distal tip electrode 70. In the example, the core wire 52 extends the entire length of the lead and is secured to the distal tip electrode, which itself is shown with a suture hole that is used in prior art methods of implantation for pulling the lead through tunneled tissue. Typically a physician would loop a suture once or several times through the suture hole and make knots to hold the suture in place for use during the pulling steps; once fully implanted, three incision methods of implantation also typically entail the physician using the suture hole to secure the lead 50 to the subcutaneous fascia. The coil 68 and proximal ring electrode 66 are each electrically coupled to one or the other of the connector rings 54, 56. Other lead designs may be used; that shown is merely illustrative.

Figure 3:
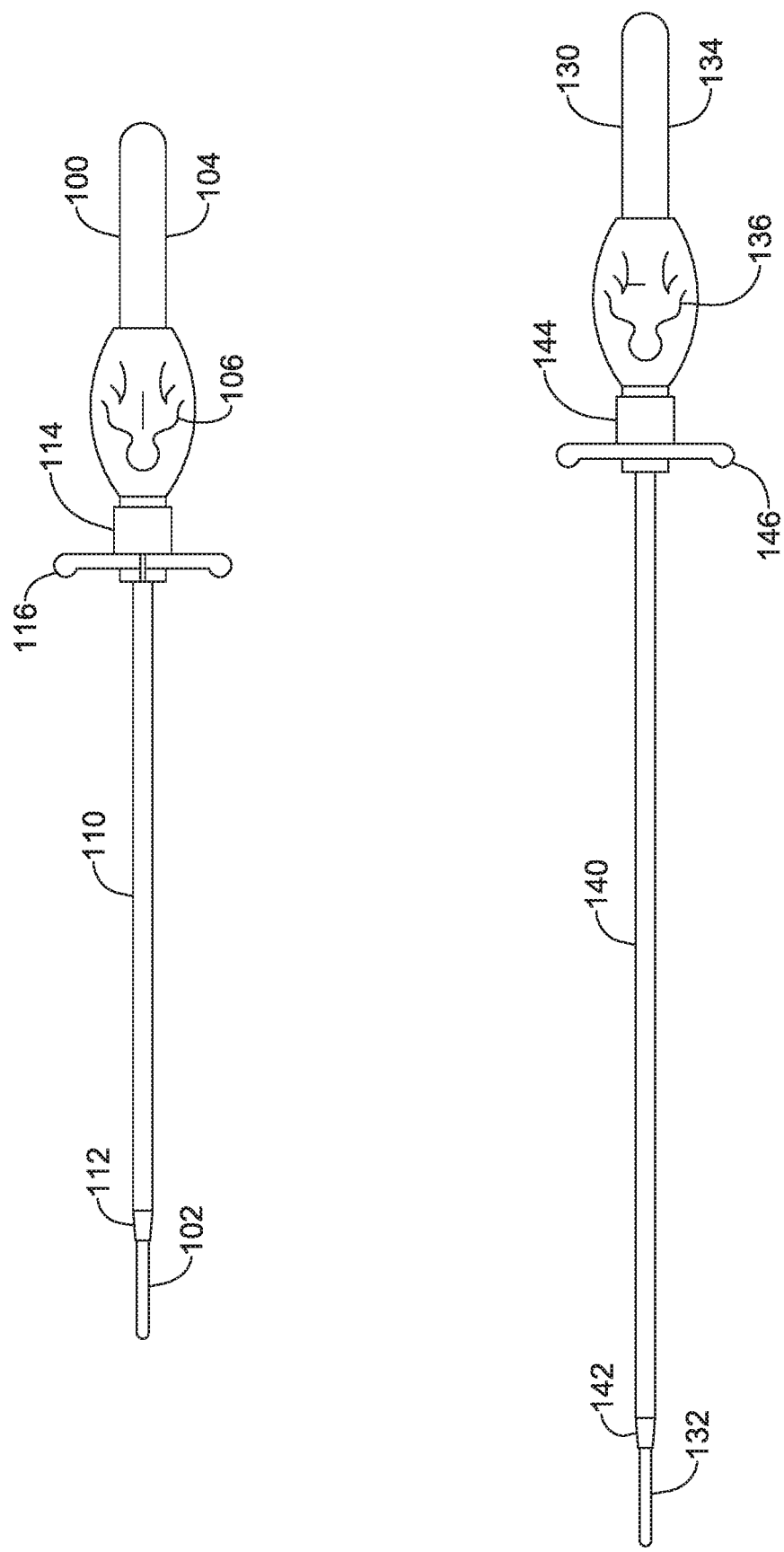
FIG. 3 shows illustrative introducer tools.

FIG. 3 shows illustrative introducer tools. An introducer tool set or kit is actually shown, with a first introducer tool 100 and a second introducer tool 130. Each of the introducer tools has a distal tunneling tip 102, 132, and a proximal handle 104, 134. For purposes of the tool set, each of the introducer tools may have a decorative indicator 106, 136 indicating which implant step the tool is designed for. For example, introducer tool 100 may have a decorative indicator 106 showing a parasternal tunnel, while introducer tool 130 may have a decorative indicator 136 showing a lateral tunnel extending between the left axilla and the xiphoid. The decorative indicators 106, 136 may be different for different use cases; or the decorative indicators 106, 136 may be omitted if desired.

Each introducer tool 100, 130 has on it a sheath 110, 140. The sheaths 110, 140 comprise distal ends 112, 142 that terminate near but proximal to the dissecting tips 102, 132 when disposed as shown. Each sheath has a proximal hub 114, 144 and splittable handle 116, 146. The hubs 114, 144 are designed to snap or screw onto corresponding structures on the handles 104, 134 of the respective tools 100, 130 to secure the sheaths 110, 140 during insertion in a patient. The splittable handles 116, 146 are known in the art and allow a user to apply a breaking force to each handle 116, 146 that will allow splitting removal of each sheath 110, 140 when desired.

It can be observed that the first introducer tool 100 is shorter than the second introducer tool 130. In an example, the first introducer tool is adapted for tunneling in a superior or cephalad direction from the xiphoid incision along the sternum or to the left of the sternum a distance of at least 10 cm. In some examples, this means that the length of the sheath is at least 10 cm, and the length of the first introducer tool 100 distal of the handle 100 and decorative indicator 106 is at least about 12 cm. In each of these respects the second introducer tool 130 may be longer. The outer diameter of the sheaths 110, 140 may be just large enough to allow the inner diameter thereof to slidingly receive a lead to be implanted. For example, an outer diameter of 2.5 to 5 mm may be used, with about 4 mm or less preferred. In a working example, the sheath inner diameter at its tip is about 3.8 mm, or 11 French, to accommodate a lead having a 9 French outer diameter.

A set of more specific dimensions follows. These dimensions are illustrative of one set of embodiments; it should be understood the invention is not limited to these dimensions unless explicitly recited in the claims. In some examples, the first introducer tool has an overall length in the range of about 25 to 30 cm, or about 28 cm in a working example, and the second introducer tool has an overall length in the range of about 30 to 50 cm, or about 39 cm in a working example. The portion of the first introducer tool 100 distal of the handle may have a length in the range of about 12 to about 20 cm, or about 17 cm in a working example, with the sheath 110 sized to leave about 1-3 cm of the distal tip of the first introducer tool 100 uncovered, or about 2.1 cm in a working example. The portion of the second introducer tool 130 distal of the handle may have a length in the range of about 20 to about 40 cm, or about 28 cm in a working example, with the sheath 140 sized to leave about 1-4 cm of the distal tip of the second introducer tool uncovered, or about 2.6 cm in a working example. Other dimensions may be used. For example, a kit may be provided with dimensions reduced (in length that is) by in the range of 20% to 50% for pediatric uses, depending on the size of the patient. A range of kits may be provided to allow, for example, a standard, extra-large, and extra small kits to be offered for different patient body types.

FIGS. 4A-4E illustrate several implantation steps and methods using tools as in FIG. 3. Starting with FIG. 4A, a patient 200 has been prepared for implantation by making an axillary incision 202 at about the left axilla (as shown, this may be the left anterior axillary line, though the midaxillary line may be used instead), and a xiphoid incision 204 near the xiphoid 206, to the left of the midline 208. An introducer tool 220 having a handle 222 and a distal tunneling tip 224 is shown as ready for insertion through the axillary incision 202, with a sheath 226 thereon.

Prior instructions for implanting the S-ICD System electrode would recite, for example, the use of approximately a 2 cm horizontal incision at the xiphoid. If desired, the incision may take the form of a puncture, having a smaller size such as in the range of 0.5 to 1.5 cm.

Turning to FIG. 4B, the introducer tool has been advanced through the axillary incision 202 to and through the xiphoid incision 204. The tool itself has been removed, leaving the sheath 226 in place, with a proximal end 228 of the sheath 226 extending out of the axillary incision 202, and a distal end 230 extending out of the xiphoid incision 204. A second introducer tool 250 is shown, ready for insertion through the xiphoid incision 204, again having a proximal handle 252, a distal tunneling tip (not numbered), and a sheath 256 having a proximal end 258 thereon.

Figure 4A:
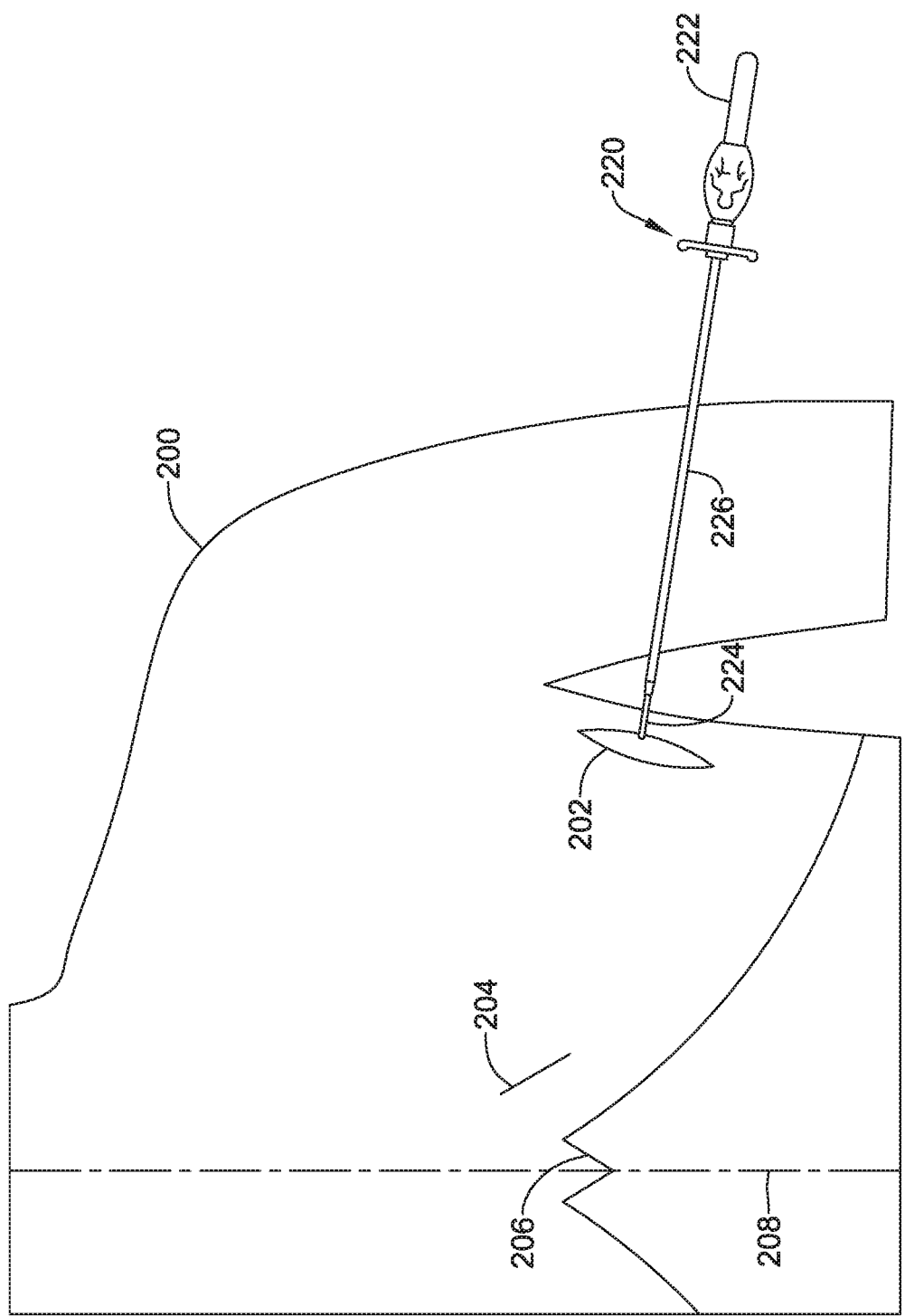
Figure 4C:
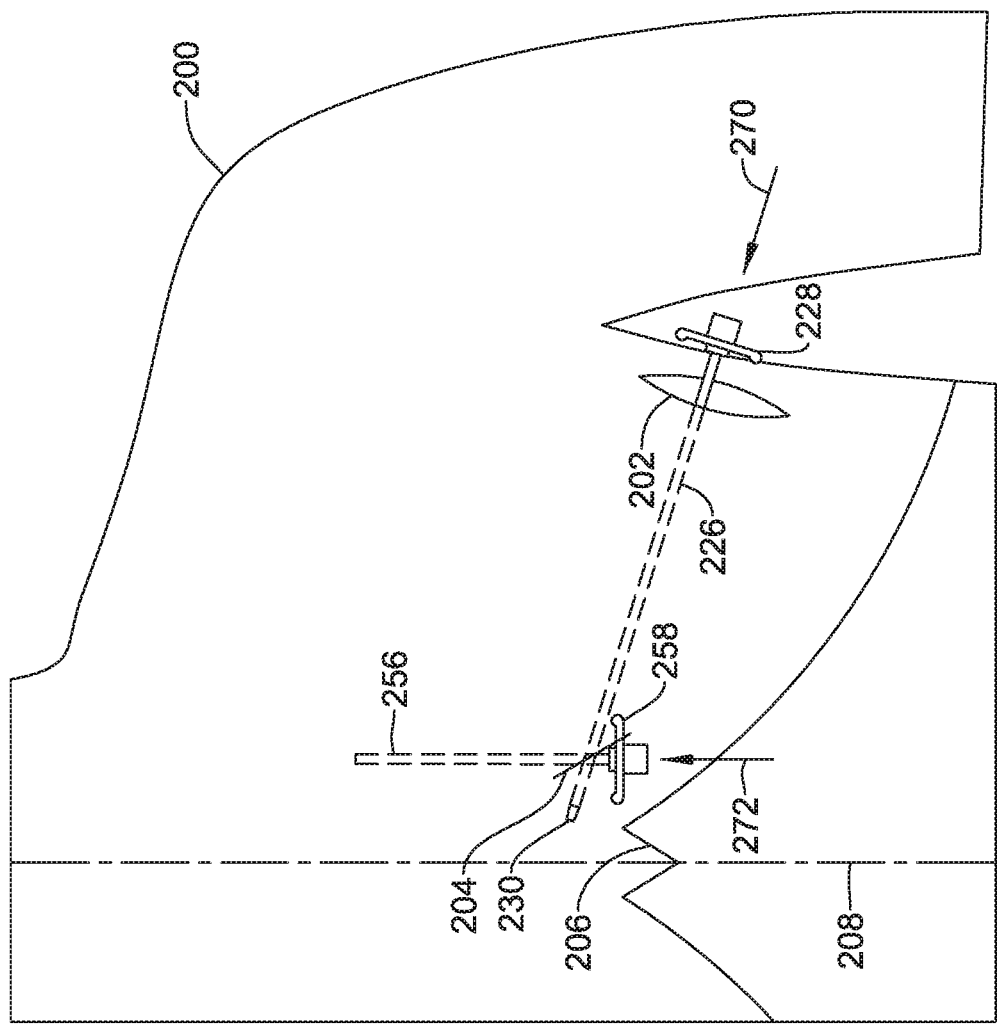

In FIG. 4C, the second introducer tool has been advanced through the xiphoid incision to create a parasternal tunnel. To do so the second introducer tool may be advanced through the xiphoid incision in a generally cephalad direction alongside or parallel to the sternum. The second introducer tool has been removed, leaving behind the sheath 256, the proximal end of which is shown near the xiphoid incision. Next, the lead is to be inserted. FIG. 4C illustrates a two-step lead insertion—a distal end of a lead is inserted via direction 270 into the proximal end 228 of the sheath 226 and advanced from the axilla to the xiphoid through sheath 226, until the distal end of the lead exits the distal end 230 of the sheath 226. If desired, the sheath 226 may be removed at this point in the procedure or, alternatively, the sheath 226 may be left in place. Next, the distal end of the lead is inserted as shown at 272 through proximal end 258 of sheath 256. Once the lead is inserted as far as it can be through the proximal end 258 of sheath 256, sheath 256 is removed.

A suture sleeve can be added to the lead for securing the lead at the xiphoid incision 204 to the patient's subcutaneous tissue, in some examples, to the fascia. If not already removed, sheath 226 can then be removed (before or after the suture sleeve is added or used).

In an alternative example, the lead may comprise its own fixation features. Such fixation features may include features at the distal tip thereof, as disclosed in U.S. Provisional Patent Application No. 62/547,187, or US PG Patent App. Pub. Nos. 20120029335 or 20170095657, the disclosures of which are incorporated herein by reference. Fixation features integral to the lead may also be provided at a position selected to correspond to the xiphoid incision, approximately, as disclosed in U.S. Provisional Patent Application No. 62/546,867, the disclosure of which is incorporated herein by reference. Additional fixation features integral to a subcutaneous lead are disclosed in US PG Patent App. Pub. No. 20040230279, the disclosure of which is incorporated herein by reference. Thus fixation may be offered along an extended portion of the length of the lead (such by expanding members, tines, etc.), at the distal end, at an intermediate position, and/or all of these. Pharmacological or other agents may be provided on the lead if desired, as suggested in US PG Patent App. Pub. No. 20040230272, the disclosure of which is incorporated herein by reference. A suture sleeve may be used or omitted, as desired, when fixation features are integral with the lead itself. In another example, a suture sleeve may be applied to a lead near the axillary incision, rather than at the xiphoid.

Once any fixation is compete at the xiphoid incision, the incision may be closed in any suitable conventional manner (suture, staple, adhesive, etc.).

With the lead placed and sheaths and tools removed, one encounters the configuration of FIG. 4E, with a lead 290 extending out of the axillary incision 202 and secured along the path shown, from axillary incision 202 to the xiphoid incision 204 and thence superiorly along the left side of the sternum (not shown). With respect to tunneling along or over the sternum, an implanting physician may direct the introducer during the prior step just over the middle of the sternum, using the sternum itself as a guide to ensure depth of the implantation procedure to keep the lead along a tissue plane directly on the fascia. In various examples, the lead 390 may thus reside over the sternum or to the left of the sternum. In an alternative, the lead 390 may be implanted to the right side of the sternum.

While the examples herein are generally directed to the use of a left-sided pulse generator implantation and, generally, to a lead implantation that is medial or just to the left of the sternum, it should be noted that for some patient anatomies the procedure may be modified to accommodate a right-sided implantation. Such may be the case for some patients with unusual anatomies such as having the heart on the right side of the torso.

Once configured as shown, an implantable pulse generator can be coupled/secured to the lead 290 at the lead proximal end. A pocket for receiving the pulse generator is formed near the axillary incision 202, and the pulse generator can be inserted therein. Typically, the pulse generator will include one or more suture attachment features that allow a physician to suture the pulse generator to the fascia in the implantation pocket.

Figure 4D:
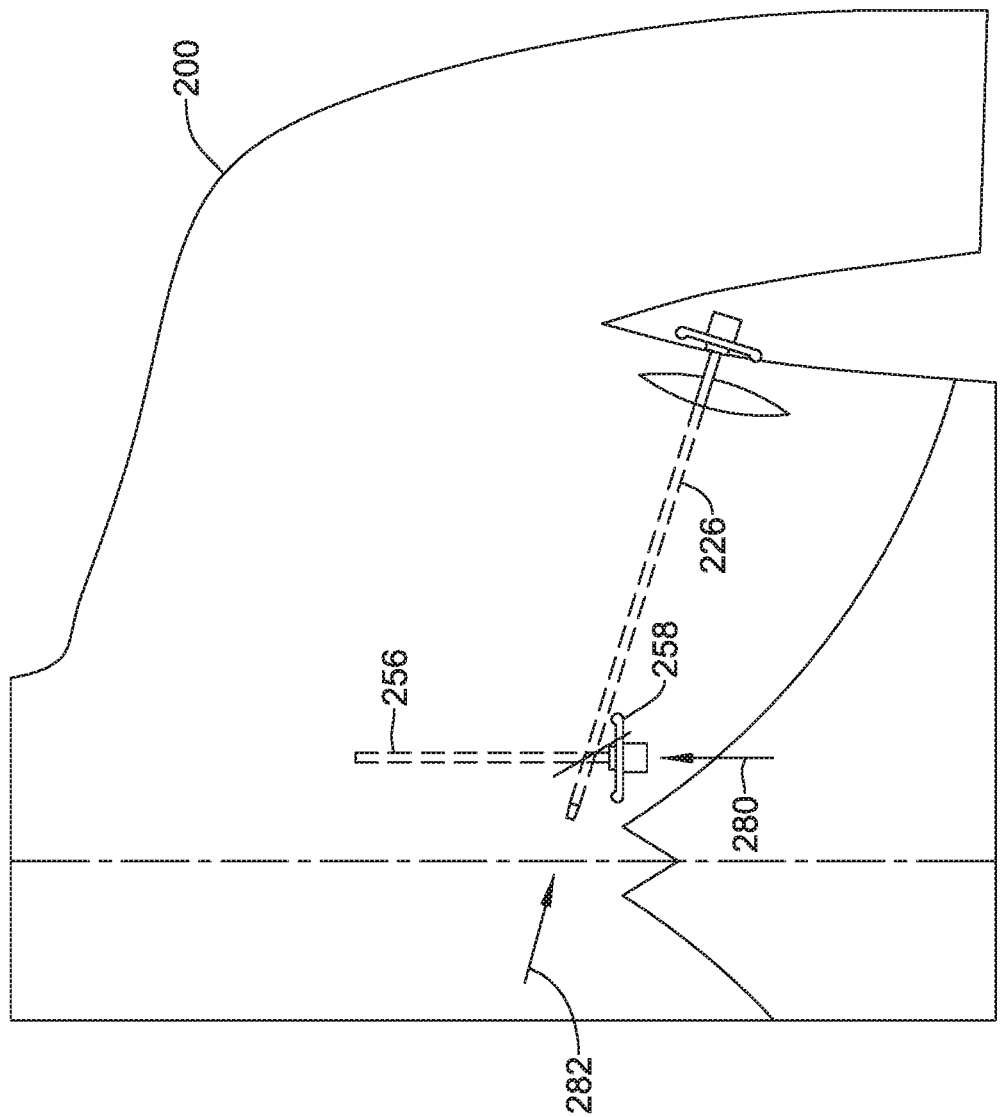

FIG. 4D shows an alternative to FIG. 4C. Here, the distal end of the lead is inserted into sheath 256 as shown by arrow 280, while the proximal end of the lead is inserted into the distal end of the sheath 226, as shown by arrow 282. In some examples, the step represented by arrow 280 is performed before the step represented by arrow 282; in other examples, the step represented by arrow 282 is performed before the step represented by arrow 280. In some examples, the sheaths 226, 256 may be removed individually as soon as the lead has been inserted therethrough. In other examples, the sheaths 226, 256 may remain in place until the lead is in its generally final position. Again, a suture sleeve may be used and/or applied to secure the lead near the xiphoid incision. Once the sheaths are removed, one is left with the configuration of FIG. 4E.

Throughout the method of FIGS. 4A-4E (regardless which of the FIG. 4C or FIG. 4D variants are used), the step of attaching a suture to the distal end of the lead for purposes of pulling the lead through tissue is omitted. This saves procedure time. Further, a physician may pull or push a lead through a sheath more quickly than a lead can be pulled through a subcutaneous tunnel, as the patient tissue around the lead is protected from tearing due to quick advancement of the lead by the presence of the sheath. Finally, the steps shown also make it easier to implant the lead by advancement of the proximal end from the xiphoid incision to the axillary incision without need for a plug or cover over the proximal end of the lead.

FIGS. 5A-5E illustrate several additional implantation steps and methods using tools as in FIG. 3. At a high level, the method is somewhat like that of FIGS. 4A-4E, except that FIG. 5A reverses the step of FIG. 4A. Starting with FIG. 5A, a patient 300 has been prepared for implantation by making an axillary incision 302 at about the left axilla (as shown, this may be the left anterior axillary line, though the midaxillary line may be used instead), and a xiphoid incision 304 near the xiphoid 306, to the left of midline 308. An introducer tool 320 having a handle 322 and a distal tunneling tip 324 is shown as ready for insertion through the xiphoid incision 304, with a sheath 326 thereon.

Turning to FIG. 5B, the introducer tool has been advanced through the xiphoid incision 304 to and through the axillary incision 304. The tool itself has been removed, leaving the sheath 326 in place, with a proximal end 328 of the sheath 326 extending out of the xiphoid incision 302, and a distal end 330 extending out of the axillary incision 304. A second introducer tool 350 is shown, ready for insertion through the xiphoid incision 304, again having a proximal handle 352, a distal tunneling tip 354, and a sheath 356 having a proximal end 358 on the second introducer tool 350.

Figure 5A:
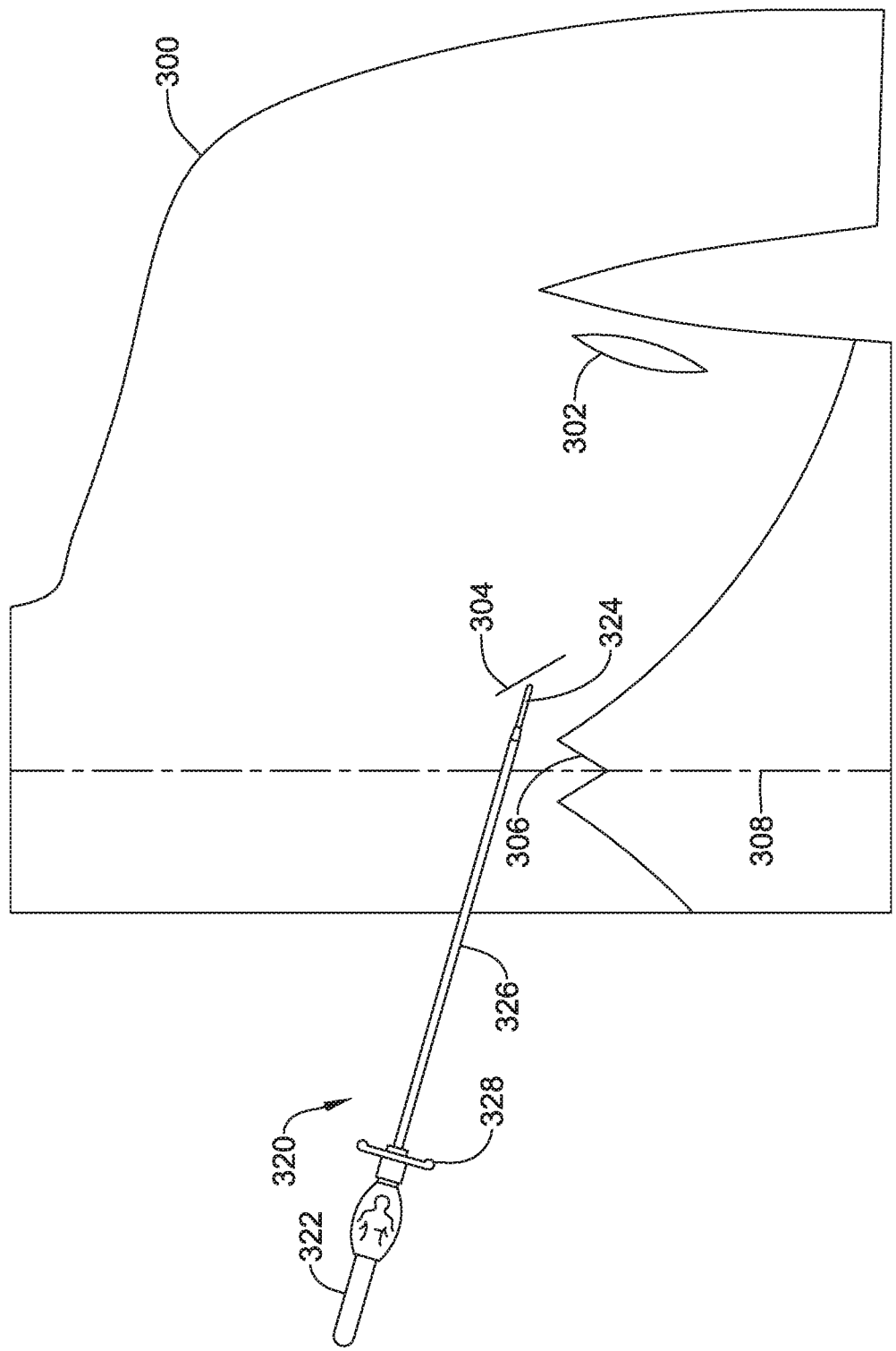
Figure 5C:
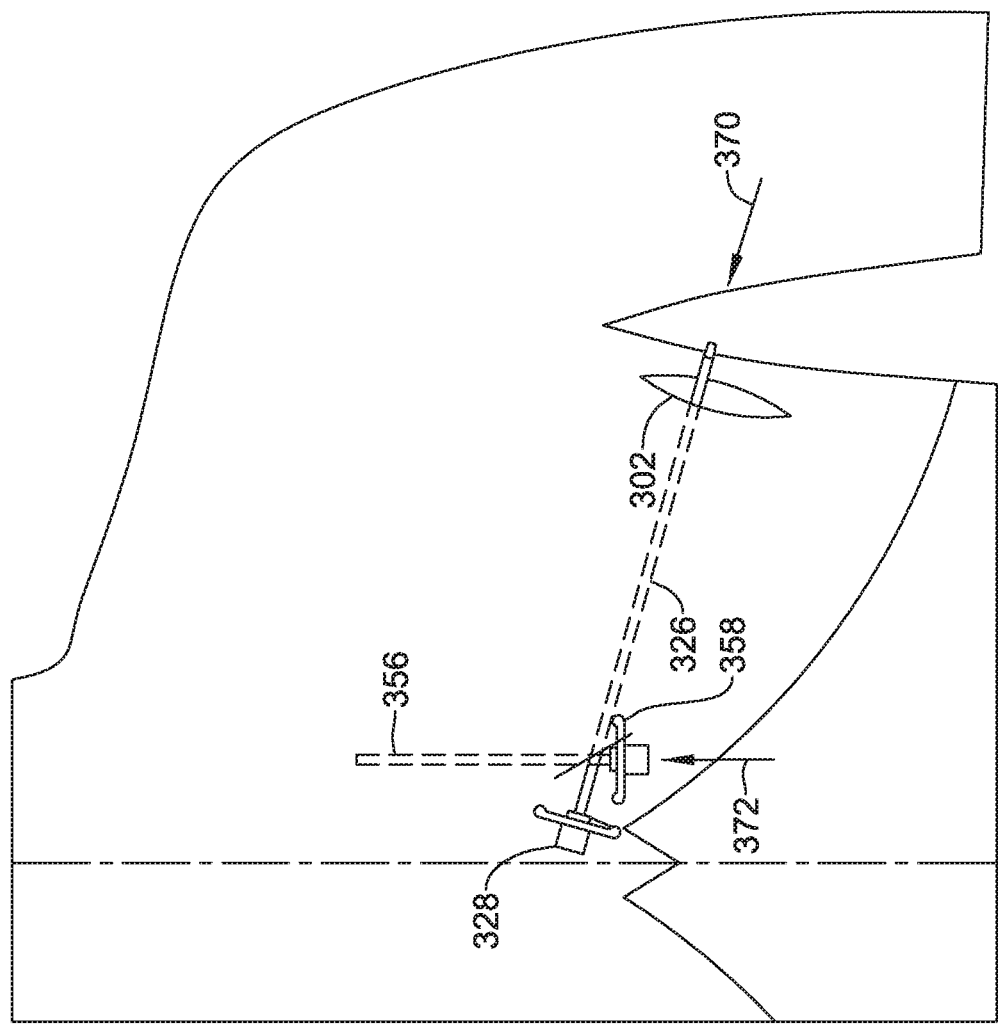

In FIG. 5C, the second introducer tool has been advanced through the xiphoid incision to create a parasternal tunnel. The second introducer tool has been removed, leaving behind the sheath 356, the proximal end of which is shown near the xiphoid incision.

Next, the lead is to be inserted. FIG. 5C illustrates a two-step lead insertion—a distal end of a lead is inserted via direction 370 into the distal end of the sheath 326 and advanced from the axilla to the xiphoid through sheath 326, until the distal end of the lead exits the proximal end 328 of the sheath 326. If desired, the sheath 326 may be removed at this point in the procedure or, alternatively, the sheath 326 may be left in place. Next, the distal end of the lead is inserted as shown at 372 through proximal end 358 of sheath 356. Once the lead is inserted as far as it can be through the proximal end 358 of sheath 356, sheath 356 is removed.

Again, as described above, suture sleeves, fixation elements and/or pharmacological agents may be included to secure the lead in a desired position. If not already removed, sheath 326 can be removed (before or after the suture sleeve is added or used). Once any fixation is compete at the xiphoid incision, the incision may be closed in any suitable conventional manner (suture, staple, adhesive, etc.).

Figure 5D:
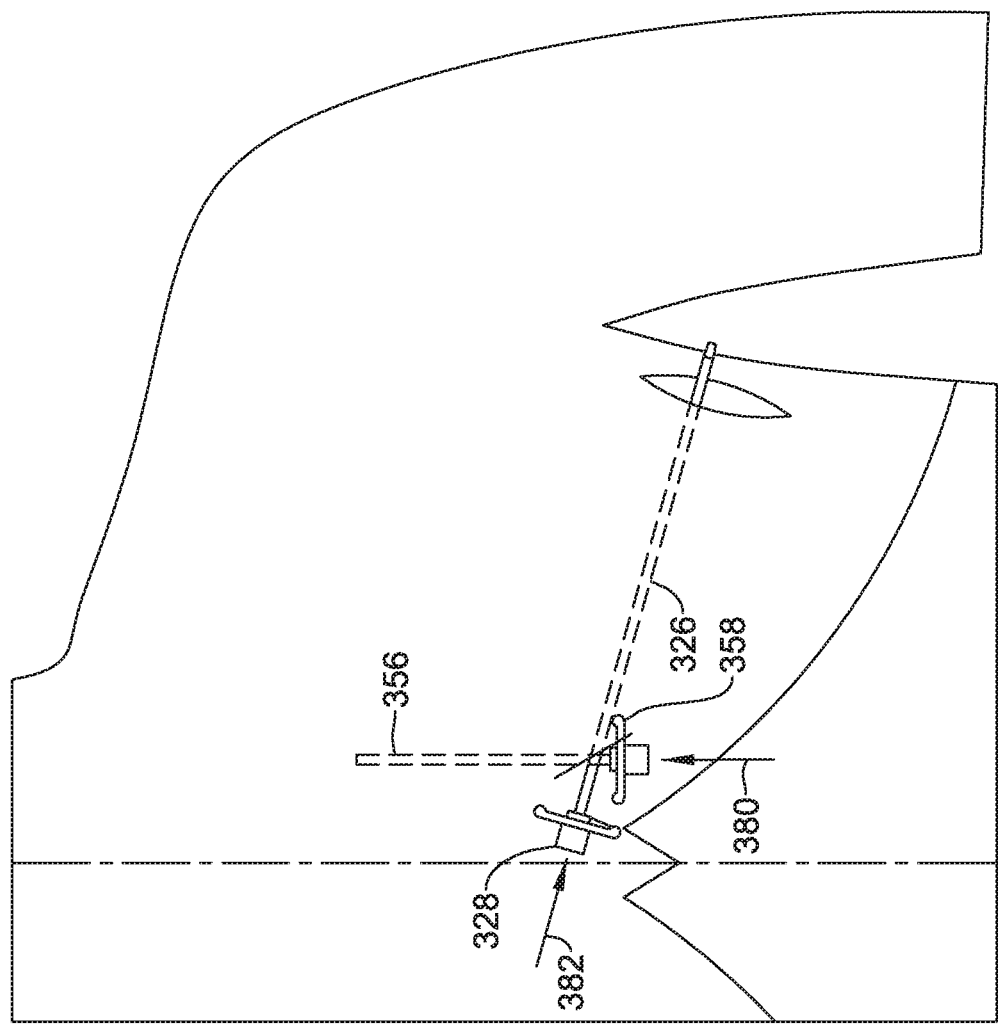
Figure 5E:
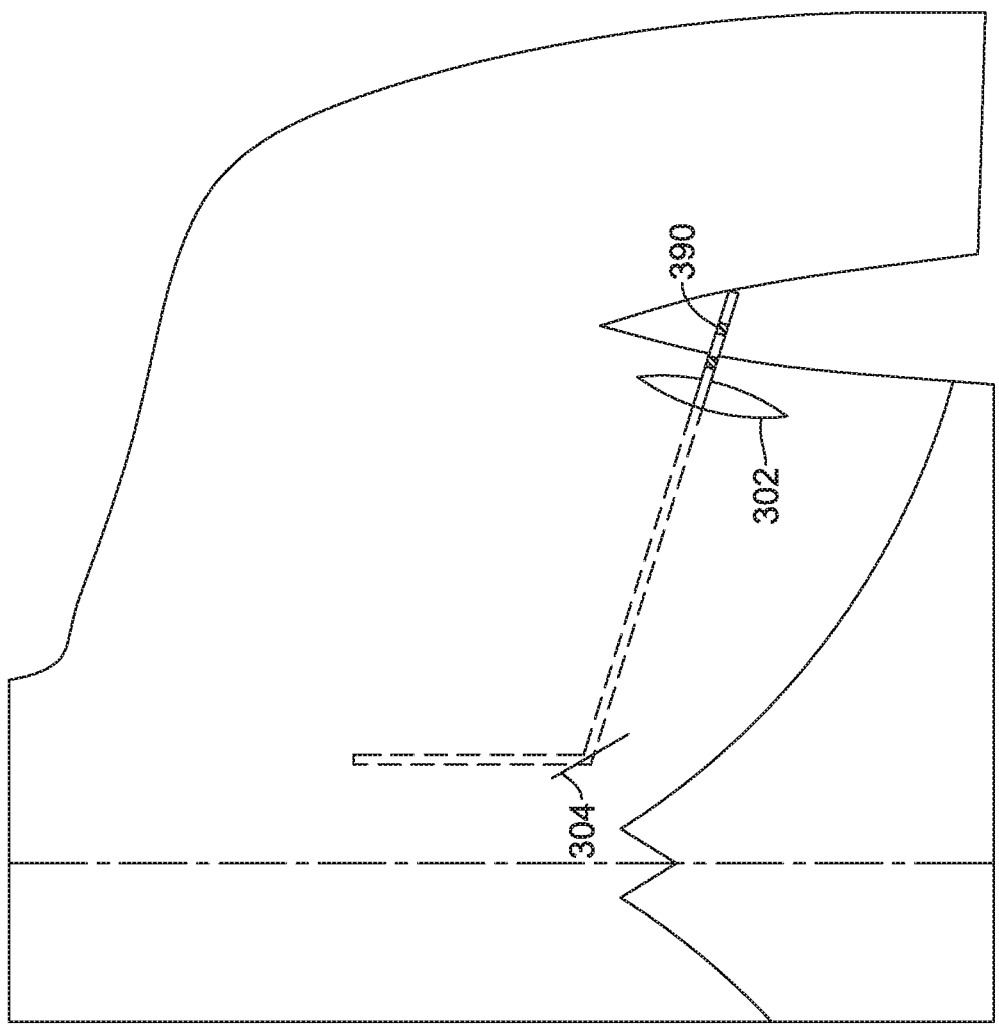

This would leave the configuration of FIG. 5E, with a lead 390 extending out of the axillary incision 302 and extending along the path shown, from axillary incision 302 to the xiphoid incision 304 and thence superiorly along the left side of the sternum (not shown). For example, an implanting physician may direct the introducer during the prior step just over the middle of the sternum, using the sternum itself as a guide to ensure depth of the implantation procedure to keep the lead along a tissue plane directly on the fascia. In various examples, the lead 390 may thus reside over the sternum or to the left of the sternum. In an alternative, the lead 390 may be implanted to the right side of the sternum.

Once configured as shown, an implantable pulse generator can be coupled/secured to the lead 390 at the lead proximal end. A pocket for receiving the pulse generator is formed near the axillary incision 302, and the pulse generator can be inserted therein. Typically, the pulse generator will include one or more suture attachment features that allow a physician to suture the pulse generator to the fascia in the implantation pocket.

FIG. 5D shows an alternative to FIG. 4C. Here, the distal end of the lead is inserted into sheath 356 as shown by arrow 380, and the proximal end of the lead is inserted into the proximal end 328 of the sheath 326, as shown by arrow 382. In some examples, the step represented by arrow 380 is performed before the step represented by arrow 382; in other examples, the step represented by arrow 382 is performed before the step represented by arrow 380. In some examples, the sheaths 326, 356 may be removed individually as soon as the lead has been inserted therethrough. In other examples, the sheaths 326, 356 may remain in place until the lead is in its generally final position. Again, a suture sleeve may be used and/or applied to secure the lead near the xiphoid incision. Once the sheaths are removed, one is left with the configuration of FIG. 5E.

Figure 6:
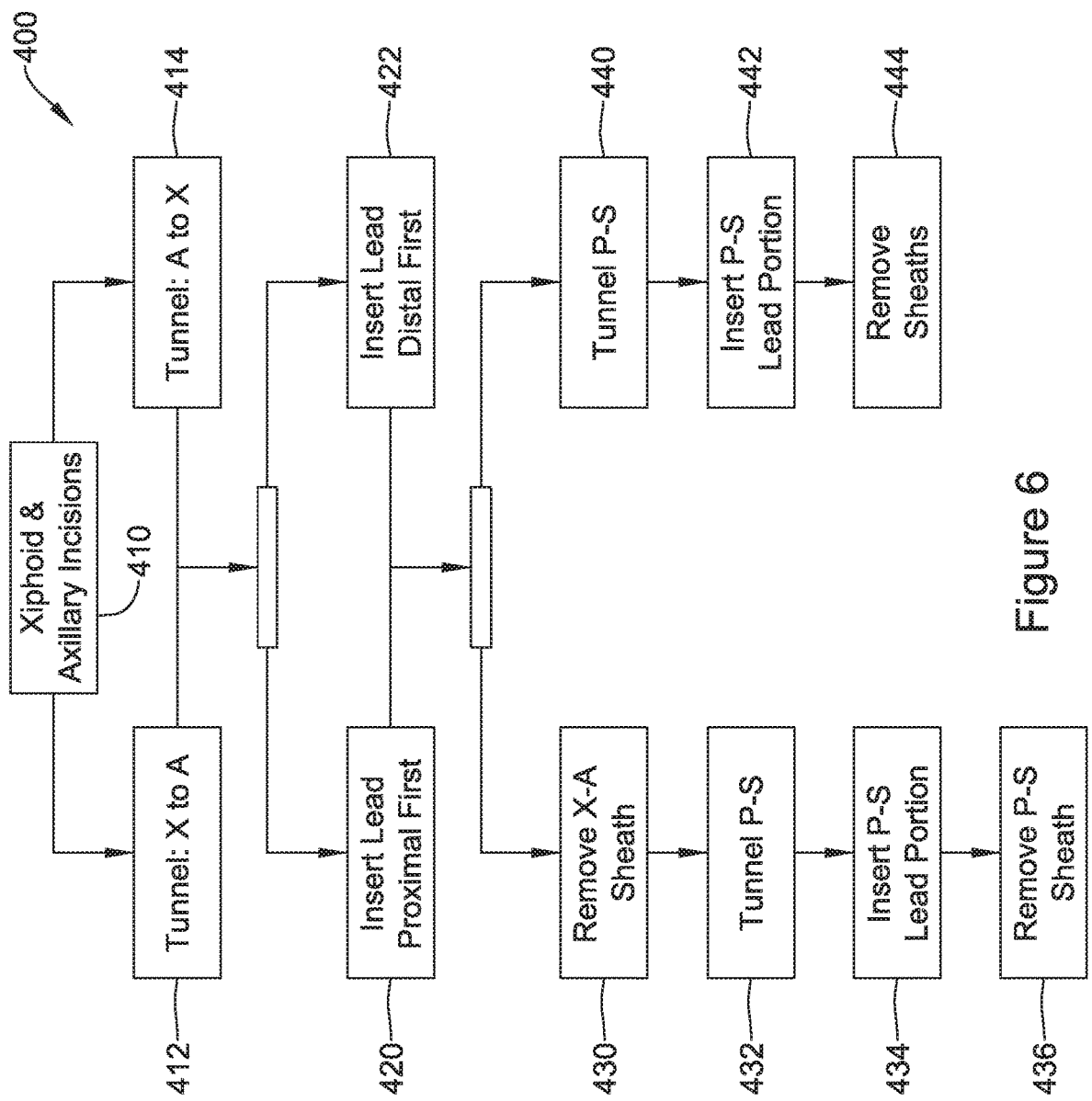
FIG. 6 shows in block flow form a number of implant methods with various options and alternatives.

FIG. 6 shows in block flow form a number of implant methods with various options and alternatives. The overall flow 400 may be understood as disclosing several separate embodiments, or may be understood as disclosing a set of options that a physician may select as part of one embodiment.

At 410, the patient is prepared for implantation by the making of xiphoid and axillary incisions. Next, the physician may tunnel from the xiphoid to the axillary incision, as indicated at 412 or, alternatively, may tunnel from the axillary incision to the xiphoid incision 414. After either of 412, 414, an introducer tool is removed from the tunnel so made, leaving behind a sheath for introduction of a lead therethrough. Next the lead can be inserted into the sheath left behind during whichever of steps 412/414 was performed. In some examples, the lead is inserted proximal end first, as indicated at 420, meaning that the proximal end of the lead would be inserted through a sheath and advanced from the xiphoid incision to the axillary incision. Alternatively, the lead may be introduced distal end first, as indicated at 422, meaning that the distal end of the lead would be inserted through a sheath and advanced from the axillary incision to the xiphoid incision.

The method then offers two separate paths. In one path, the sheath that was left behind after performance of either of 412, 414 is removed, as indicated at 430. A parasternal tunnel ("P-S") is then formed, as indicated at 432, which would be performed by inserting an introducer tool having a sheath thereon through the xiphoid incision alongside the sternum. Removal of the sheath at 430 prior to performing step 432 may be beneficial insofar as fewer surgical instruments may then be present at the xiphoid for starting the next tunneling step. Block 432 includes each of making the parasternal tunnel and withdrawing the introducer tool while leaving the sheath behind. The portion the lead that will reside in the parasternal tunnel is then inserted as indicated at 434 through the sheath left behind in block 432. Finally, the sheath in the parasternal tunnel is removed as indicated at 436.

It should be pointed out that block 430 may be performed after any combination of blocks 412/414 and 420/422. Thus, for example, these method flows are disclosed:

410-412-420-430-432-434-436
    410-412-422-430-432-434-436
    410-414-420-430-432-434-436
    410-414-422-430-432-434-436

Steps of applying additional sutures, activating any fixation structures and/or applying sutures sleeves can also be performed at suitable points in the procedure. Typically one may apply the suture sleeve (if used) to a lead before the sheaths have all been removed as security against the sheath removal dislodging anything, but this is not required.

Going back up the chart, block 440 is an alternative to block 430. Here, the parasternal tunnel is formed as indicated at 440, without first removing the sheath that maintains the tunnel between xiphoid and axilla. Again, block 440 includes each of making the parasternal tunnel and withdrawing the introducer tool while leaving the sheath behind. The portion the lead that will reside in the parasternal tunnel is then inserted as indicated at 442 through the sheath left behind in block 440. Finally, the sheaths are removed, in any suitable order, as indicated at 444. The physician will want to take care to ensure that the lead distal tip is not disturbed as the sheaths are removed.

Again, block 440 may be performed after any combination of blocks 412/414 and 420/422. Thus, for example, these method flows are disclosed:

410-412-420-440-442-444
    410-412-422-440-442-444
    410-414-420-440-442-444
    410-414-422-440-442-444

Steps of applying additional sutures, activating any fixation structures and/or applying sutures sleeves can also be performed at suitable points in the procedure. Typically one may apply the suture sleeve (if used) to a lead before the sheaths have all been removed as security against the sheath removal dislodging anything, but this is not required. As before, once the lead is placed an implantable pulse generator can be attached near the left axillary incision, and all the incisions can then be closed.

In one example, a user performs the method according to a flow of 410, then either 412 or 414, as the user prefers, then 422 (or alternatively 420), and then 440, 442, 444, with the sheaths removed last of all. In another example, instead, the user flow is 410, then either 412 or 414, as user prefers, then 440, at which point the lead introducer tools are removed, followed by 422 and 442, finally with block 444 to remove the sheaths last of all. In such an approach, the tunneling steps precede all lead placement, such that the tunneling and sheath placement are completed and the introducer tools removed prior to the lead placement starting.

Figure 7:
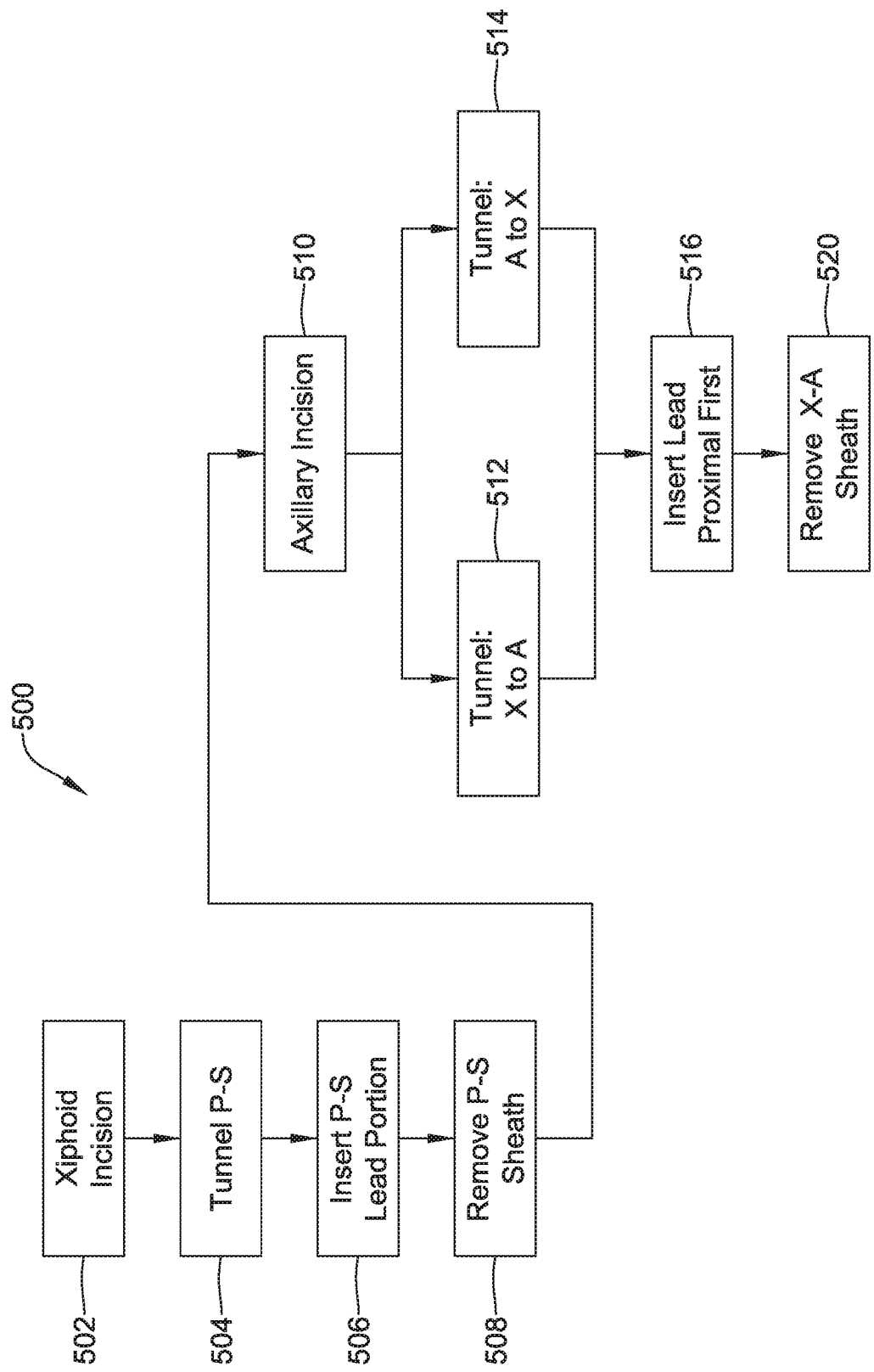
FIG. 7 shows in block flow form another set of implant methods with various options and alternatives.

FIG. 7 shows in block flow form another set of implant methods with various options and alternatives. The method here places the distal portion of the lead first during the procedure. One benefit here may be that the distal part of the lead, which has various extra structures that can serve as traps for microbes, is exposed to the surgical environment for a reduced period of time, reducing the risk of infection.

In the example 500, the xiphoid incision only is made first, as indicated at 502. The parasternal tunnel is formed at 504, using an introducer tool having a sheath thereon. Block 504 includes making the tunnel and removing the introducer tool while leaving the sheath behind in the formed tunnel. Next, the parasternal portion of the lead is inserted at indicated at 506, and the parasternal sheath left behind at block 504 is removed, as indicated at 508. In some examples, these steps are performed first with a lead that has integral distal attachment features such as tines or hooks, as discussed above, though a lead having no such fixation may also be used in the example 500. If desired, a suture sleeve may be applied to the lead and secured to the fascia following step 508 to help ensure that the distal end of the lead in the parasternal tunnel is not dislodge by any subsequent steps.

Next, the axillary incision is made at 510. Here, there are two options. A tunnel may be formed by insertion of an introducer tool, with a sheath on it again, through the xiphoid incision toward the axillary incision as indicated at 512. Alternatively, the tunnel may be formed by insertion of the introducer tool/sheath through the xiphoid incision toward the axillary incision as indicated at 514.

Regardless which of 512 or 514 is performed, the next step is to insert the proximal end of the lead into the sheath, as indicated at 516. If block 512 was performed, then in block 516 the proximal end of the lead will enter the proximal end of the sheath; if block 514 was performed, then in block 516 the proximal end of the lead will enter the distal end of the sheath. Finally, as indicated at 520, the sheath left behind during the tunneling step 512/514 is removed.

Steps of applying additional sutures, activating any fixation structures and/or applying sutures sleeves can also be performed at suitable points in the procedure. If not applied after block 508, a suture sleeve may be applied. As before, once the lead is placed an implantable pulse generator can be attached near the left axillary incision, and all the incisions can then be closed.

In any of the above examples, once the physical implantation is complete, the typical procedure concludes with diagnostic and operational testing, which may include setting up, for example, sensing configurations and setting therapy rules. Induction testing may be performed as well, to observe device performance and efficacy.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a subcutaneous-only defibrillator system in a patient, the system comprising a pulse generator having a lead port and a lead having a proximal end to attach to the pulse generator lead port and a distal end with at least one electrode thereon, the method comprising:
   making an axillary incision near the left axilla;
   making a xiphoid incision near the xiphoid;
   inserting a first introducer tool and first sheath, with the first sheath removably disposed on the first introducer tool, through one of the axilla or xiphoid incisions to create a first tunnel to the other of the xiphoid or axilla incisions;

removing the first introducer tool and leaving the first sheath in place between the axilla and xiphoid incisions;

inserting the proximal end of the lead into the first sheath and advancing the proximal end of the lead from the xiphoid incision to and through the axillary incision through the first sheath;

removing the first sheath while maintaining the lead in a position such that the proximal end of the lead extends out of the axillary incision and the distal end of the lead extends out of the xiphoid incision with a portion of the lead disposed in the first tunnel;

inserting a second introducer tool and second sheath, with the second sheath removably disposed on the second introducer tool, through the xiphoid incision in a generally cephalad direction to create a second tunnel alongside or parallel to the sternum;

removing the second introducer tool and leaving the second sheath in place in the second tunnel;

inserting the distal end of the lead into the second sheath and advancing the distal end of the lead to a desired position; and removing the second sheath while maintaining a portion of the lead in the second tunnel.

2. The method of claim 1 wherein:

the first introducer tool has a proximal end with a handle and a tunneling shaft extending from the handle to a distal tip;

the first sheath has a proximal end with a hub and a distal end having a length such that, when the first sheath is removably disposed on the first introducer tool, the hub is adjacent the handle and the distal end of the first sheath is proximal of the distal tip of the first introducer tool;

the step of inserting the first introducer tool and the first sheath is performed by inserting the distal end of the first introducer tool into the axillary incision and advancing the distal end of the first introducer tool to and through the xiphoid incision until the distal end of the first sheath extends out of the xiphoid incision; and the step of inserting the proximal end of the lead into the first sheath is performed by passing the proximal end of the lead through the distal end of the first sheath and advancing the lead therein until the proximal end of the lead extends out of the hub of the first sheath and the axillary incision.

3. The method of claim 1 wherein:

the first introducer tool has a proximal end with a handle and a tunneling shaft extending from the handle to a distal tip;

the first sheath has a proximal end with a hub and a distal end having a length such that, when the first sheath is removably disposed on the first introducer tool, the hub is adjacent the handle and the distal end of the first sheath is proximal of the distal tip of the first introducer tool;

the step of inserting the first introducer tool and the first sheath is performed by inserting the distal end of the first introducer tool into the xiphoid incision and advancing the distal end of the first introducer tool to and through the axillary incision until the distal end of the first sheath extends out of the axillary incision; and the step of inserting the proximal end of the lead into the first sheath is performed by passing the proximal end of the lead through the hub of the first sheath and advancing the lead therein until the proximal end of the lead extends out of the distal end of the first sheath and the axillary incision.

4. The method of claim 1 further comprising using one or more sutures to secure the lead in place at the xiphoid incision.

5. The method of claim 1 wherein the lead comprises one or more anchoring structures thereon at an intermediate location between the at least one electrode and the proximal end, the anchoring structure configured to anchor the lead in position near the xiphoid incision.

6. The method of claim 5 further comprising applying one or more sutures at the anchoring structure to anchor the lead in position at the xiphoid incision.

7. The method of claim 5 wherein the anchoring structure includes one or more tines or hooks extending therefrom to secure to patient tissue for holding the lead in a desired position.

8. The method of claim 1 wherein the lead comprises one or more anchoring structures at the distal tip thereof, the anchoring structures comprising one or more of a tine or a hook.

9. The method of claim 1 wherein the step of removing the first sheath is performed after the step of inserting the distal end of the lead into the second sheath.

10. A method of implanting a subcutaneous-only defibrillator system in a patient, the system comprising a pulse generator having a lead port and a lead having a proximal end to attach to the pulse generator lead port and a distal end with at least one electrode thereon, the method comprising:

making an axillary incision near the left axilla;

making a xiphoid incision near the xiphoid;

inserting a first introducer tool and first sheath, with the first sheath removably disposed on the first introducer tool, through one of the axilla or xiphoid incisions to create a first tunnel to the other of the xiphoid or axilla incisions;

removing the first introducer tool and leaving the first sheath in place between the axilla and xiphoid incisions;

inserting the distal end of the lead into the first sheath and advancing the distal end of the lead from the axillary incision to and through the xiphoid incision through the first sheath;

removing the first sheath while maintaining the lead in a position such that the proximal end of the lead extends out of the axillary incision and the distal end of the lead extends out of the xiphoid incision with a portion of the lead disposed in the first tunnel;

inserting a second introducer tool and second sheath, with the second sheath removably disposed on the second introducer tool, through the xiphoid incision in a generally cephalad direction to create a second tunnel alongside or parallel to the sternum;

removing the second introducer tool and leaving the second sheath in place in the second tunnel;

inserting the distal end of the lead into the second sheath and advancing the distal end of the lead to a desired position; and removing the second sheath while maintaining a portion of the lead in the second tunnel.

11. The method of claim 10 wherein:

the first introducer tool has a proximal end with a handle and a tunneling shaft extending from the handle to a distal tip;

the first sheath has a proximal end with a hub and a distal end having a length such that, when the first sheath is removably disposed on the first introducer tool, the hub is adjacent the handle and the distal end of the first sheath is proximal of the distal tip of the first introducer tool;

the step of inserting the first introducer tool and the first sheath is performed by inserting the distal end of the first introducer tool into the axillary incision and advancing the distal end of the first introducer tool to and through the xiphoid incision until the distal end of the first sheath extends out of the xiphoid incision; and the step of inserting the distal end of the lead into the first sheath is performed by passing the distal end of the lead through the hub of the first sheath and advancing the lead therein until the distal end of the lead extends out of the distal end of the first sheath and the xiphoid incision.

12. The method of claim 10 wherein:

the first introducer tool has a proximal end with a handle and a tunneling shaft extending from the handle to a distal tip;

the first sheath has a proximal end with a hub and a distal end having a length such that, when the first sheath is removably disposed on the first introducer tool, the hub is adjacent the handle and the distal end of the first sheath is proximal of the distal tip of the first introducer tool;

the step of inserting the first introducer tool and the first sheath is performed by inserting the distal end of the first introducer tool into the xiphoid incision and advancing the distal end of the first introducer tool to and through the axillary incision until the distal end of the first sheath extends out of the axillary incision; and the step of inserting the distal end of the lead into the first sheath is performed by passing the distal end of the lead into the distal end of the first sheath and advancing the lead therein until the distal end of the lead extends out of the hub of the first sheath and the axillary incision.

13. The method of claim 10 further comprising using one or more sutures to secure the lead in place at the xiphoid incision.

14. The method of claim 10 wherein the lead comprises one or more anchoring structures thereon at an intermediate location between the at least one electrode and the proximal end, the anchoring structure configured to anchor the lead in position near the xiphoid incision.

15. The method of claim 14 further comprising applying one or more sutures at the anchoring structure to anchor the lead in position at the xiphoid incision.

16. The method of claim 14 wherein the anchoring structure includes one or more tines or hooks extending therefrom to secure to patient tissue for holding the lead in a desired position.

17. The method of claim 10 wherein the lead comprises one or more anchoring structures at the distal tip thereof, the anchoring structures comprising one or more of a tine or a hook.

18. The method of claim 10 wherein the step of removing the first sheath is performed after the step of inserting the distal end of the lead into the second sheath.

19. An implantation tool kit for implantation of a medical device comprising:

a first introducer tool having a proximal end with a handle and a tunneling shaft extending from the handle to a distal tip, the tunneling shaft having a first length;

a first sheath having a proximal end with a hub and a distal end and having a second length such that, when the first sheath is removably disposed on the first introducer tool, the hub is adjacent the handle and the distal end of the first sheath is proximal of the distal tip of the first introducer tool;

a second introducer tool having a proximal end with a handle and a tunneling shaft extending from the handle to a distal tip, the tunneling shaft having a third length; and a second sheath having a proximal end with a hub and a distal end and having a fourth length such that, when the second sheath is removably disposed on the second introducer tool, the hub is adjacent the handle and the distal end of the second sheath is proximal of the distal tip of the second introducer tool;

wherein the first length is greater than the second length.

20. The tool kit of claim 19 wherein:

the first length is adapted for use in establishing a first tunnel from a position near the xiphoid to the left axilla of a patient, and the handle of the first introducer tool includes a marking designating that the first introducer tool is for use in establishing the first tunnel; and the second length is adapted for use in establishing a second tunnel from a position near the xiphoid cephalad within a patient for at least 10 cm, and the handle of the second introducer tool includes a marking designating that the second introducer tool is for use in establishing the second tunnel.

* * * * *